United States Patent [19]

Lu et al.

[11] Patent Number: 6,058,352
[45] Date of Patent: May 2, 2000

[54] ACCURATE TISSUE INJURY ASSESSMENT USING HYBRID NEURAL NETWORK ANALYSIS

[75] Inventors: Taiwei Lu, Petaluma; Robert A. Lieberman, Torrance, both of Calif.

[73] Assignee: Physical Optics Corporation, Torrance, Calif.

[21] Appl. No.: 08/900,319

[22] Filed: Jul. 25, 1997

[51] Int. Cl.$^7$ .................................................. G06F 17/00
[52] U.S. Cl. .............................. 702/28; 702/32; 702/183; 706/924
[58] Field of Search ................................. 702/28, 19–23, 702/27, 30–32, 38, 40, 134, 135, 139, 159, 170, 172, 183, 189, FOR 115–FOR 118, FOR 145–FOR 149, FOR 170, FOR 171; 128/925, 920, 922, 924; 600/407, 408, 477, 310, 410, 473, 476; 356/326, 328, 346, 355, 302, 303; 706/10, 20, 28, 924; 364/528.01; 382/133, 156–159; 700/48

[56] References Cited

U.S. PATENT DOCUMENTS

| | | | |
|---|---|---|---|
| 5,267,151 | 11/1993 | Ham et al. | 128/922 |
| 5,553,616 | 9/1996 | Ham et al. | 706/924 |
| 5,660,181 | 8/1997 | Ho et al. | 600/408 |
| 5,687,716 | 11/1997 | Kaufmann et al. | 706/924 |
| 5,701,902 | 12/1997 | Vari et al. | 600/473 |

OTHER PUBLICATIONS

Ham et al., Improved Detection of Biological Substances Using A Hybrid Neural Network and Infrared Absorption Spectroscopy, IEEE, pp. I–227 to I–232, 1991 (No Month).

Brochure: "SSMART Analyzers for Intelligent Instrumentation"(Physicial Optics Corporation 1995)–(No Month).
"Burn Depth Estimation—Man or Machine", David M. Heimback, M.D., et al., The Journal of Trauma, vol. 24, No. 5, pp. 373–378, May 1984.
"An Introduction to Computing with Neural Nets", Richard P. Lippmann, ASSP Magazine, pp. 4–22, Apr., 1987.
"Neural Network Model Using Interpattern Association", Taiwei Lu et al., Applied Optics, vol. 29, No. 2, pp. 284–288, Jan., 1990.
"Self–Organizing Optical Neural Network for Unsupervised Learning", Taiwei Lu et al., Optical Engineering, vol. 29, No. 9, pp. 1107–1113, Sep. 1990.
"Optical $N^4$ Implementation of Two–Dimensional Wavelet Transform", Yunlong Sheng et al., Optical Engineering, vol. 31, No. 9, pp. 1859–1863, Sep., 1992.
"Spectroscopy and Hybrid Neural Network Analysis", Taiwei Lu et al., Physical Optics Corporation Paper, pp. 1–25. (No Date).

*Primary Examiner*—Hal Wachsman
*Attorney, Agent, or Firm*—Nilles & Nilles, S.C.

[57] ABSTRACT

Systems and methods using a neural network based portable absorption spectrometer system for real-time automatic evaluation of tissue injury are described. An apparatus includes an electromagnetic signal generator; an optical fiber connected to the electromagnetic signal generator; a fiber optic probe connected to the optical fiber; a broad band spectrometer connected to the fiber optic probe; and a hybrid neural network connected to the broad band spectrometer. The hybrid neural network includes a principle component analyzer of broad band spectral data obtained from said broad band spectrometer.

13 Claims, 3 Drawing Sheets

ACCURATE TISSUE INJURY ASSESSMENT USING HYBRID NEURAL NETWORK ANALYSIS

BACKGROUND OF THE INVENTION

1. Field of the Invention

The present invention relates generally to the field of tissue injury analysis. More particularly, the present invention relates to a method and apparatus for objective tissue injury analysis. Specifically, a preferred embodiment of the present invention relates to the use of a fiber optic probe, a spectrometer and a hybrid neural network to increase the accuracy of tissue injury analysis. The present invention thus relates to a method and apparatus for tissue injury analysis of the type that can be termed objective.

2. Discussion of the Related Art

Within this application several publications are referenced by. The disclosures of all these publications in their entireties are hereby expressly incorporated by reference into the present application for the purposes of indicating the background of the present invention and illustrating the state of the art.

Tissue injury is common in daily life. For example, approximately 70,000 serious burn cases are reported in the United States every year, at a cost to the economy of an estimated two billion dollars. Traditionally, burns have been classified as first, second, or third degree, based on visual criteria. First degree burns are visually indicated by redness and blistering of the skin. Second degree burns are visually indicated by withering of the skin without charring. Third degree burns are visually indicated by eschar formation and charring.

This type of classification, which has been used with only minor alterations for nearly two hundred years, is concerned chiefly with the intensity of burning and not with the depth of tissue destroyed. Only recently have burn physicians come to realize that the depth of injury is of greater importance than superficial appearance. The classification of burns that has recently been adopted has completely forsaken all reference to outward appearances, which are only an indication of the severity of surface burning. The new type of classification recognizes two degrees of burn injury. The first new classification is partial thickness skin loss, implying the presence of sufficient living epithelial elements to resurface the area. The second new classification is full-thickness skin loss, implying virtually complete destruction of all epithelial elements so that healing can only occur by contraction of the wound and epithelial cell migration from the edge of the wound or by surgical intervention.

Proper treatment depends on the correct classification of the burn. Further, early differentiation between these two degrees of burns is critical for several reasons. It is better to excise dead tissue and close the wound than to allow spontaneous separation of the slough, with its attendant risks of infection, fibrosis, and loss of function. Surgical results are best when the proper treatment is taken within the shortest time. The sooner a definite diagnosis is made, the sooner the patient with partial-thickness burns can leave the hospital, decreasing costs for both the hospital and the patient. In life-threatening burns, when donor sites are at a premium, it is very important to distinguish quickly between full-thickness and partial-thickness burn injuries.

FIG. 1 shows a model of a three dimensional section of human skin. Two major tissue layers are conventionally recognized as constituting human skin 5. The outer layer is a thin stratified epithelium, called the epidermis 10, which varies relatively little in thickness over most of the body. The human epidermis is typically between 75 μm and 150 μm thick. Underlying the epidermis 10 is a dense layer of fibrous elastic connective tissue, called the dermis 20, which constitutes the mass of skin. The dermis 20 supports extensive vascular and nerve networks, and encloses specialized excretory and secretory glands and keratinized appendage structures such as hair and nail. Beneath the skin is the subcutaneous tissue, or hypodermis 50, which is variously composed of loose areolar connective tissue or fatty connective tissue displaying substantial regional variations in thickness. Nerves 25 pass through the hypodermis 50. Of particular interest is the presence and depth of hair follicles 30 and sweat glands 40 in the dermis. The bases of these structures are surrounded by cells capable of forming new "skin." These cells lie very close to the interface of the dermis and the subcutaneous fat 60, and represent the vital plane insofar as spontaneous skin repair is concerned. If destruction occurs below this vital plane, the burn is a full-thickness burn; if above this vital plane, it is a partial-thickness burn.

The blood supply in the skin comes from cutaneous branches of the subcutaneous musculocutaneous arteries. Branches arising from the cutaneous arteries give rise to a distinctive small vessel plexus which lies deep in the dermis near and parallel to the interface with the subcutaneous tissue. Therefore, destruction of a large area of hair follicles and sweat glands in a full-thickness burn devascularizes the skin in the same area. This is the basis of several previous burn diagnosis methods that use the new type of classification.

However, classifying a burn is not easy immediately after the burn occurs, and usually depends upon intuition about the appearance of the burn rather than upon accurate description and definition (i.e., objective characterization). Early visual assessment may be difficult because the ability of the wound to heal depends strongly on the condition of underlying tissues, which in the case of severe burns are generally obscured by overlying layers of dead and denatured skin. Thus, three days after burns were incurred, the surgeons in one study were only willing to commit themselves to a predication in about two thirds of the cases. Heimbach, D. M., Afromowitz, M. A., Engrav, L. H., Marvin, J. A. and Perry, B., "Burn Depth Estimation: Man or Machine," The Journal of Trauma, vol. 24, No. 5, pp. 373–378 (1984). One fourth of the predictions made at this time were incorrect. In an effort to address this problem many objective diagnostic methods have been proposed by previous researches. These methods take information from the surface, as well as beneath the skin, and depend on the following criteria and procedures. One method depends on a fluorescein test for the presence of dermal circulation. Another method depends on staining reactions on the surface of the burn. Another method depends on sensitivity of the burn to pinprick. Yet another method depends on temperature variations within the burn area as evidenced by thermogram.

Although some progress has been made in laboratory testing, heretofore, no method has gained widespread clinical acceptance. The limitations of previous methods include poor burn depth predictive values on various selected days post-burn, excessive cost, cumbersome techniques, time-consuming techniques and techniques that often include a toxic reaction.

These previous methods can be classified either as invasive or non-invasive. The invasive methods include the fluorescence test, staining appearance and sensitivity to pinprick. The non-invasive approaches are the thermogram imaging and multispectral photographic analysis.

The fluorescence method employs a fluorometer to quantify fluorescence as a measure of burn depth. However, the fluorescein injected into the femoral vein in this method causes a toxic reaction in some patients. Green, H. A., Bua, D., Anderson, R. R. and Nishioka, N. S., "Burn Depth Estimation Using Indocyanine Green Fluorescence." Arch Dermatol, vol. 128, January, pp. 43–49 (1992).

The staining reaction method introduced by Patey and Scarff maps out areas of surface necrosis using dyes such as hematoxylin, marking the absence of blood circulation. Patey, D. H. and Scarff, R. W., British Journal of Surgeon, vol. 32, pp. 32 (1944). However, this method reveals nothing about skin layers deeper than the eye can see, whereas the critical layer in burns under the new type of classification is the deepest plane of living epithelial elements.

While the pin-prick method is self-explanatory, it is often inaccurate in predicting the depth of a burn. In addition, this method can result in significant blood loss. Jackson, D. M., "In Search of an Acceptable Burn Classification." British Journal of Plastic Surgeon, vol. 23, pp. 118–145 (1970).

Thermography, the measurement of the infrared waves emitted by all objects, is time consuming in that it usually requires at least 20 minutes in an air-conditioned room. Mladick, R., Georgiade, N. and Thorne, F., "A Clinical Evaluation of the Use of Thermography in Determining Degree of Burn Injury." Plastic and Reconstructive Surgery, Vol. 38, No. 6, pp. 512–518 (1966). Further, thermography devices are very costly.

Anselmo and Zawacki developed a method based on rationing the magnitudes of visible and infrared radiation from several spectral ranges. Anselmo, V. J. and Zawacki, B. E., "Multispectral Photographic Analysis: A new Quantitative Tool to Assist in the Early Diagnosis of Thermal Burn Depth." Annals of Biomedical Engineering, Vol. 5, pp. 179–193 (1977). Although their results were promising, the analysis time was too slow for clinical decision making.

Heimbach developed a burn depth estimation approach called the Burn Depth Indicator (BDI) method. Heimbach, D. M., Afromowitz, M. A., Engrav, L. H., Marvin, J. A. and Perry, B., "Burn Depth Estimation: Man or Machine," The Journal of Trauma, vol. 24, No. 5, pp. 373–378 (1984); Lu, T., Lerner, J., "Spectroscopy and Hybrid Neural Networks," to appear in the Proceedings of the IEEE, April, 1996; Lerner, J. M., Lu, M. Angel and K. Kyle, Enhancing Minimum Detection Levels of Chlorinated Hydrocarbons: One Example of the Power of Neural Net Assisted Spectroscopy, American Laboratory, September, 1993. It is similar to the method of Anselmo and Zawacki (relating burn depth to the ratios of red/green, red/infrared, and green/infrared light reflected from the burn wound), but is much faster. This approach is based on the premise that the reflectance intensity of different optical wavelength ranges corresponds to different degrees of burns, and more specifically on the premise that green and red light are important for partial-thickness burns and red and infrared are important for full-thickness burns. Heimbach's experimental results show that the BDI method is significantly more accurate than clinical assessment in cases where surgeons subjectively predicted burn injuries would not heal. The BDI method is reported to have maintained an accuracy of 79% for wounds for which the surgeons would not make a prediction.

However, limited data analysis techniques allowed Heimbach to choose only the average intensity in each of several specific frequency ranges. This may have restricted the prediction accuracy and the application of the BDI method because the details of these frequency ranges may be different for different degrees of burn even though their averages are nearly the same. Further, other frequency ranges may also contain information about the classification of a burn injury.

Other tissue injuries for which better assessment accuracy is needed include contusions, bed sores and subdural hematoma and skin cancer. Other areas in which improved assessment accuracy is needed include monitoring skin for signs of skin cancer and characterizing biological tissues in general for blood perfusion, oxygenation and arterial blood gas levels.

SUMMARY AND OBJECTS OF THE INVENTION

By way of summary, the present invention is directed to hybrid neural network analysis of a broad band spectrum from a tissue injury. The invention includes an advanced signal processing capability which includes a hybrid neural network that is specifically designed to extract broad band spectral features from burn spectra collected by a spectrometer that is optimized for burn depth classification. The hybrid neural network may be implemented using conventional neural network software, such as the SSMART Analysis™ package. ("SSMART Analysis" is a trademark of Physical Optics Corporation, Torrance Calif.) An unexpected effect of the present invention, which is a substantial improvement, is to increase the accuracy of tissue injury analysis.

A primary object of the invention is to provide an apparatus that accurately classifies tissue injuries. Another object of the invention is to provide an apparatus that is cost effective. It is another object of the invention to provide an apparatus that is rugged and reliable, thereby decreasing down time and operating costs. It is yet another object of the invention to provide an apparatus that has one or more of the characteristics discussed above but which is relatively simple to manufacture and assemble using a minimum of equipment.

In accordance with a first aspect of the invention, these objects are achieved by providing an apparatus comprising: an electromagnetic signal generator; an optical fiber connected to said electromagnetic signal generator; a fiber optic probe connected to said optical fiber; a broad band spectrometer connected to said fiber optic probe; and a hybrid neural network connected to said broad band spectrometer, wherein said hybrid neural network includes a principle component analyzer of broad band spectral data obtained from the broad band spectrometer. In one embodiment, said hybrid neural network includes: an autoscaling processor; a singular value decomposition analyzer; and a neural network classifier.

Another object of the invention is to provide a method that can be used to accurately analyze tissue injuries. It is another object of the invention to provide a method that is predictable and reproducible, thereby decreasing variance and operating costs. It is yet another object of the invention to provide a method that has one or more of the characteristics discussed above but which is relatively simple to setup and operate using moderately skilled workers.

In accordance with a second aspect of the invention, these objects are achieved by providing a method comprising: providing an electromagnetic signal generator; an optical fiber connected to said electromagnetic signal generator; a fiber optic probe connected to said optical fiber; a broad band spectrometer connected to said fiber optic probe; a hybrid neural network connected to said broad band spectrometer; and an output device connected to said hybrid neural network, said output device displaying a representation; positioning said fiber optic probe proximal an object to be analyzed; transmitting a first electromagnetic signal to said object from said electromagnetic signal generator; conveying a second electromagnetic signal from said object to said broad band spectrometer; transforming said second electromagnetic energy signal from said object into a broad band spectrum with said broad band spectrometer; transmitting said broad band spectrum from said broad band spectrometer to said hybrid neural network; processing said broad band spectrum with said hybrid neural network to obtain an autoscaling of said broad band spectrum; processing said autoscaling of said broad band spectrum with said hybrid neural network to obtain a principal component analysis of said broad band spectrum by extracting a set of orthogonal feature vectors to represent said broad band spectrum; classifying said set of orthogonal feature vectors with said hybrid neural network to obtain a set of results; and transforming said representation to display said set of results. In one embodiment, positioning includes contacting said object to be analyzed with said fiber optic probe.

These, and other, aspects and objects of the present invention will be better appreciated and understood when considered in conjunction with the following description and the accompanying drawings. It should be understood, however, that the following description, while indicating preferred embodiments of the present invention and numerous specific details thereof, is given by way of illustration and not of limitation. Many changes and modifications may be made within the scope of the present invention without departing from the spirit thereof, and the invention includes all such modifications.

BRIEF DESCRIPTION OF THE DRAWINGS

A clear conception of the advantages and features constituting the present invention, and of the construction and operation of typical mechanisms provided with the present invention, will become more readily apparent by referring to the exemplary, and therefore nonlimiting, embodiments illustrated in the drawings accompanying and forming a part of this specification, wherein like reference numerals designate the same elements in the several views, and in which.

DESCRIPTION OF PREFERRED EMBODIMENTS

The present invention and the various features and advantageous details thereof are explained more fully with reference to the nonlimiting embodiments that are illustrated in the accompanying drawings and detailed in the following description. Descriptions of well known components and processing techniques are omitted so as to not unnecessarily obscure the present invention in detail.

1. System Overview

The present invention includes is directed to a tissue injury classification method based on information from the whole spectrum (i.e., from the ultraviolet through the visible to the near-infrared). Advanced signal processing techniques are unexpectedly effective in identifying the specific information from such a broad band spectrum that distinguishes full-thickness from partial-thickness burns.

2. Detailed Description of Preferred Embodiments

The present invention includes a system that uses a hybrid neural network to classify tissue injuries such as, for example, partial-thickness and full-thickness skin loss due to burns by analyzing multiple wavelengths in the visible and near-infrared ranges (i.e., from 500 nm to 1030 nm). The invention can also analyze wavelengths in the UV range.

Figure 1:
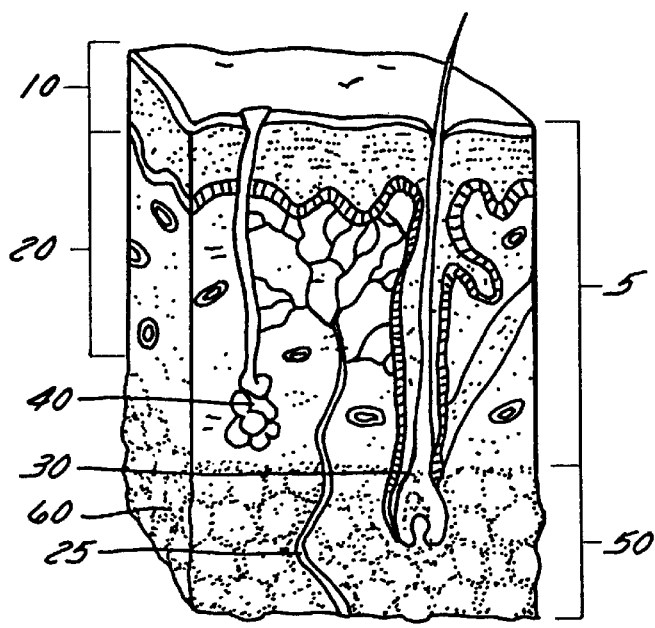
FIG. 1 illustrates an isometric sectional view of human skin, appropriately labeled "PRIOR ART"
Figure 2:
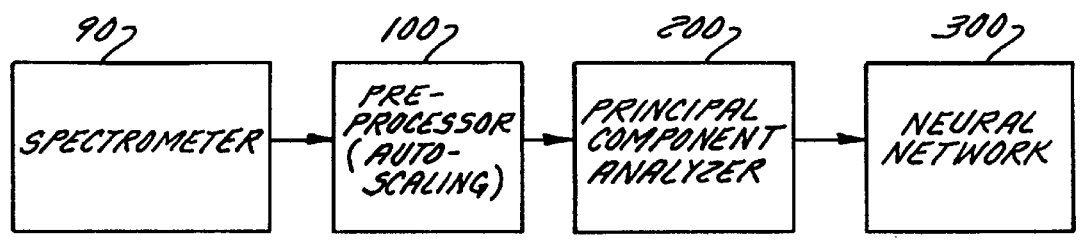
FIG. 2 illustrates a block diagram view of a flow of spectral signal processing by a hybrid neural network according to the present invention.

Referring to FIG. 2, a spectrometer 90 that can include UV, visible and near infrared (IR) capabilities is combined with a hybrid neural network for tissue injury spectral analysis that involves three procedures; preprocessing 100 (autoscaling), principal component analysis 200, and back propagation neural network processing 300. Each procedure is explained in detail in this section.

Preprocessing

Figure 6:
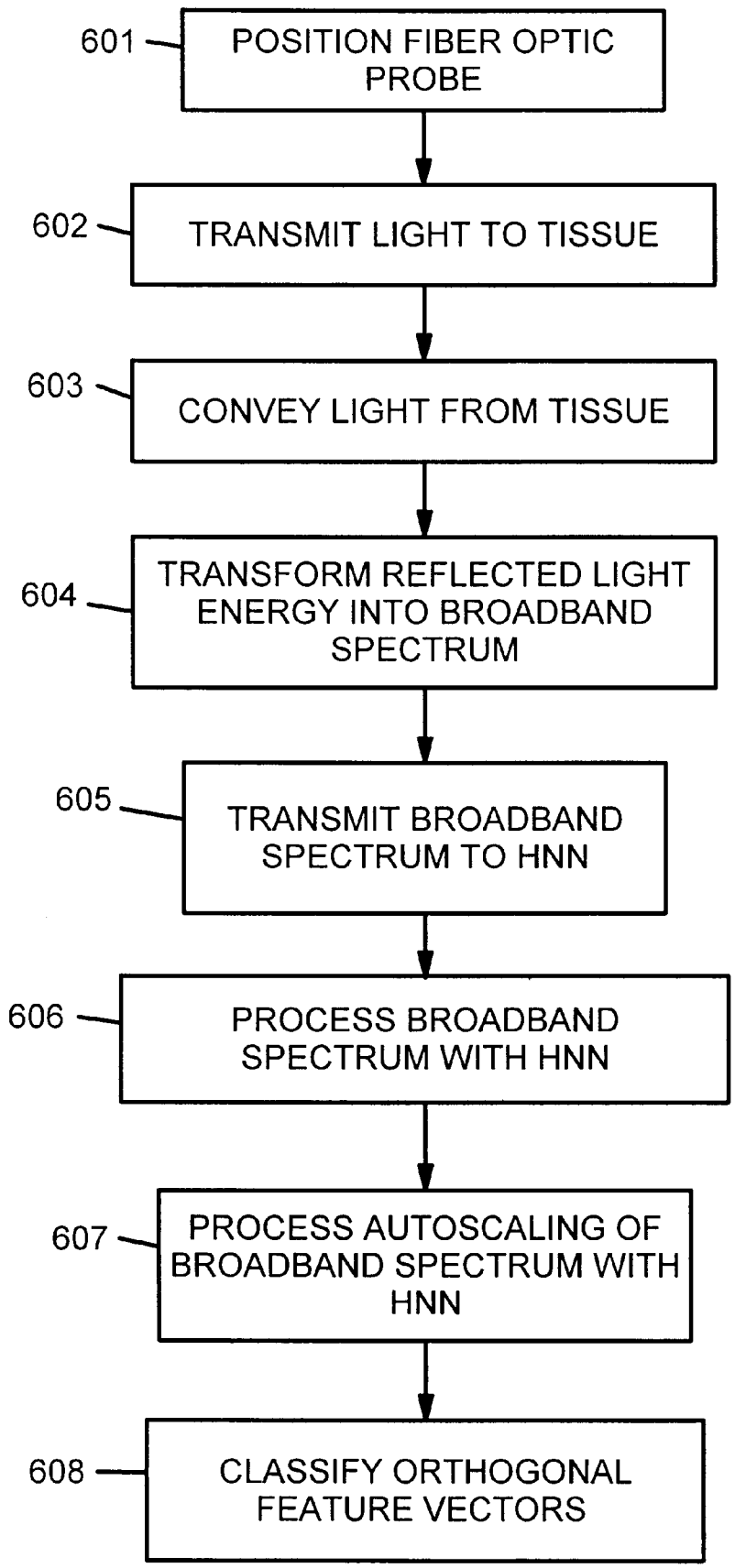
FIG. 6 is a flowchart showing a method of analyzing a tissue injury according to the present invention.

Referring now also to FIG. 6, a preferred method of analyzing an injury to a tissue is described. The method starts with positioning a fiber optic probe proximate the tissue to be analyzed (step 601), transmitting an electromagnetic signal to the tissue from an electromagnetic signal generator (step 602), conveying a second electromagnetic signal from the tissue to a broadband spectrometer (step 603), transforming the second electromagnetic signal into a broadband spectrum with the broadband spectrometer (step 604), and transmitting the broadband spectrum from the broadband spectrometer to the hybrid neural network (step 605).

Once a broad band spectrum is provided by a broad band spectrometer, it is preprocessed by autoscaling (step 606), because the amplitudes of the data sets vary according to the adjustment of the acquisition instrument and the distance and angle between the sensor and the tissue wound area. The absolute values of the intensities of individual wavelengths are not significant. The mean and variance of each spectrum (i.e., the mean wavelength intensity and the variance of the wavelength intensities) can be calculated as follows:

$$mean = \frac{1}{N}\sum_{i=0}^{N-1} x_i \quad (1)$$

$$variance = \frac{1}{N-1}\sum_{i=0}^{N-1} (x_i - mean)^2 \quad (2)$$

where $x_i$ is the input data (i.e., the intensity of a particular wavelength in the spectrum) and N is the number of samples in that spectrum. After autoscaling, the output data $y_i$ can be computed as follows:

$$y_i = \frac{x_i - mean}{\sqrt{variance}} \qquad (3)$$

After autoscaling, the output for every spectrum has a zero mean and unit variance.

Principal Component Analysis (PCA)

PCA (K-L transform) is widely used in signal and image processing for data compression and feature extraction. Especially in the field of analytical chemistry, PCA is commonly employed to distinguish different chemical compounds within a single spectrum. When the number of data sets is large, PCA is very effective for dimension reduction. There are two main reasons for using PCA to deal with tissue injury spectra. First, the acquired spectrum of each tissue injury can include a large number of data points, for example one to ten thousand data points, preferably approximately 1024 or 2048 data points, most of which are often redundant. It is not practical to use all of this data in the neural networks for pattern recognition. Second, screening spectra for such tissue injuries as, for example, full-thickness and partial-thickness burn injuries, typically reveals no obvious peaks that can be used for characterization (e.g., depth of burn). Therefore, it is very difficult to extract information from any specific frequency range to distinguish between different characterizations.

PCA (step 607) involves transforming a block of data in one representation to another representation in which a large fraction of its total energy is contained in relatively few transform coefficients. The representation dimensions ("bases") are all orthogonal after transformation. They are called "eigen-spectra." Each input spectrum can be projected onto these orthogonal bases and its corresponding coefficients can be calculated to represent the spectrum in the transformed domain. Of several methods that can be used to implement PCA, the method of singular value decomposition (SVD) is well suited to find the principal components of the data set for the purpose of implementing the present invention.

Singular value decomposition is based on a theorem of linear algebra. This theorem that states any matrix A of M×N (i.e., M rows by N columns), with M>N, can be written as a product of an M×N column-orthonormal matrix U, and M×N diagonal matrix W with non-negative elements, and the transpose of an N×N orthonormal matrix V, i.e., $$A = U W V^T, \qquad (4)$$

where the superscript T represents the transposition of a matrix and the matrix A is the spectrum data matrix.

The column vectors of $V^T$, or the row vectors of V, can be regarded as the orthonormal bases of an N-dimensional vector space. In view of Equation (4), the matrix $$B = A V = U W \qquad (4a)$$

then represents the projection of A onto $V^T$ (V), with the projection strength on the I-th base given by the I-th element $w_{ii}$ of W. Small projections of A on some vector bases of $V^T$ can be ignored because they are dominated by noise or round-off error in the data matrix A. The small projections can be removed by setting one or many smallest elements of W to zero. This procedure creates a trimmed version of W which will be referred to as $W_1$. The matrix $$B_1 = U W_1 \qquad (5)$$

then preserves all major projections of A onto $V^T$; therefore, the column vectors of $B_1$ are called the principal components of the original matrix A. Upon performing the PCA, the original data matrix A is transformed to a lower-dimensional matrix $B_1$, with noise and error removed to a certain level.

After PCA, each spectrum is represented by fewer coefficients. However, the fact that these coefficients have different scales can reduce the speed of the subsequent neural network training. Another autoscaling step is applied to these coefficients, making the neural network training much faster.

Neural Network Processing

Figure 3:
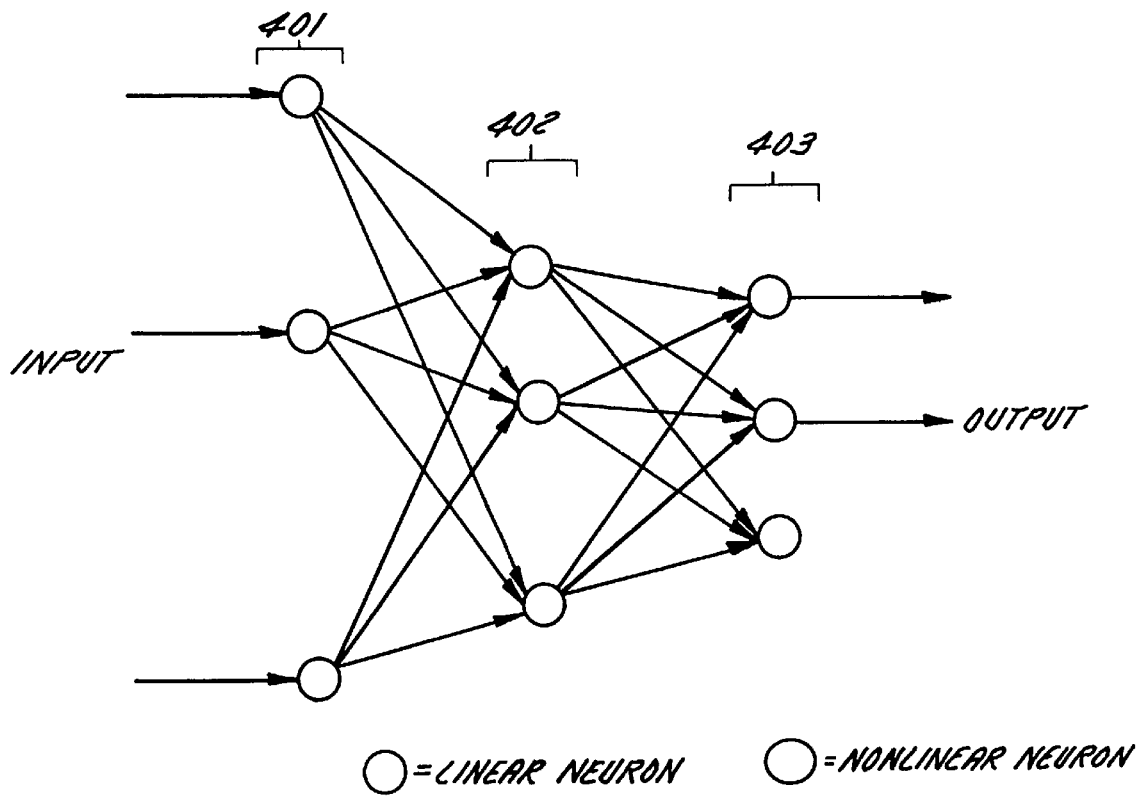
FIG. 3 illustrates a schematic diagram view of a back propagation neural network structure according to the present invention.

Artificial neural networks are very popular in pattern recognition, control engineering, and communication. Lu, T., Lerner, J., "Spectroscopy and Hybrid Neural Networks," to appear in the Proceedings of the IEEE, April, 1996; Lerner, J. M., Lu, M. Angel and K. Kyle, Enhancing Minimum Detection Levels of Chlorinated Hydrocarbons: One Example of the Power of Neural Net Assisted Spectroscopy, American Laboratory, September, 1993; Lippmann, R. P., "An Introduction to Computing with Neural Nets," IEEE Assp. Mag. pp. 4–22 (1987); Lu, T., Y. Sheng, and H. J. Caulfield, "Optical N4 Implementation of 2-D Wavelet Transform," Optical Engineering, Vol. 31, No. 9, pp. 1859–1864 (1992); Lu, T., X. Xu, S. Wu, and F. T. S. Yu, "Neural Network Model Using Interpattern Association," Appl. Opt., 29, 2, 284 (1990); Lu, T., F. T. S. Yu, and D. A. Gregory, "Self-Organizing Optical Neural Network for Unsupervised Learning," Optical Eng., 29, 9, 1107 (1990). FIG. 3 shows the structure of a two layer back propagation neural network (BPNN) (step 608). Because of their simplicity, BPNNs are in common use in pattern recognition applications. Inputs to the network are passed to each neuron in the first layer 401. The outputs of the first layer neurons then become inputs to the second layer 402, and so on. The outputs of the network are therefore the outputs of the neurons in the final layer 403. All of the neurons in a layer are normally fully connected to the neurons in adjacent layers, but there is normally no connection among neurons within a layer and normally no connecting bridging layers. The input-output relationship between any two connected neurons is determined by the connection weight $W_i$, a biased input parameter $\theta$, and another nonlinear activation function $f(\bullet)$, as follows:

$$y = f(\Sigma W_i x_i + \theta), \qquad (6)$$

where $x_i$ are the neuron inputs and y is the neuron output. The activation function $f(\bullet)$ for each hidden and output neuron is usually a sigmoid function, $$y = f(u) = \frac{1}{1 + e^{-u}} \qquad (7)$$

where u is the neuron input $$u = \Sigma W_i x_i + \theta \qquad (8)$$

The activation for each input neuron is specifically chosen to be linear.

The neural network learns from training samples to associate output characteristics with potentially complex combinations of features in the input. Adaptive learning, massive interconnection, and nonlinear classification capabilities make neural networks generally very robust to noise and distortion, and more sensitive for signal identification and classification than conventional methods. A BPNN is a good choice to perform nonlinear transformation and to recognize spectra of different classes of tissue injuries. The inputs to the neural network are the coefficients of the PCA output. The outputs from the neural network correspond to tissue injury categories, such as, for example, burn classifications.

3. Specific Spectroscopic Tissue Injury Analysis System

Figure 4:
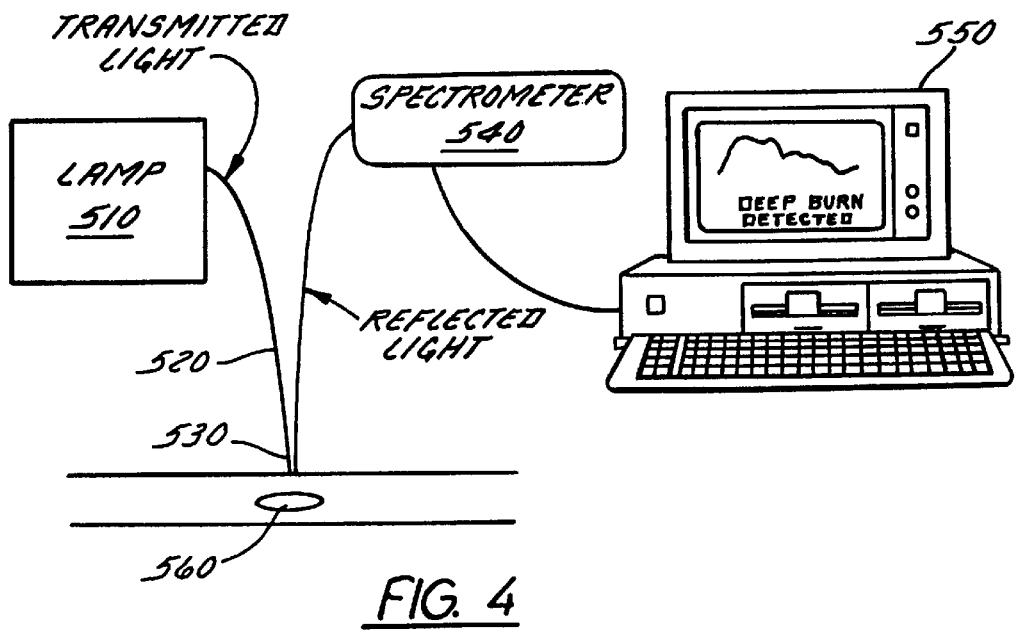
FIG. 4 illustrates a schematic view of a neural network based portable tissue injury analyzer system according to the present invention.

To describe the invention with regard to a specific embodiment, the following discussion addresses many aspects of a system that is optimized for burn analysis without in anyway limiting the invention to specific injuries, or corresponding spectral wavelengths. Referring to FIG. 4, a spectroscopic burn analysis system is shown. The system includes a tungsten halogen lamp 510 (a broad band UV, visible and near infrared light source), an optical fiber 520, an optical probe 530, a fiber optical spectrometer 540 and data acquisition and hybrid neural network processing software running on a personal computer 550. In operation, optical probe 530 is located near burned skin 560. The system is portable and easily operated, and takes only one second to acquire each spectrum.

Figure 5:
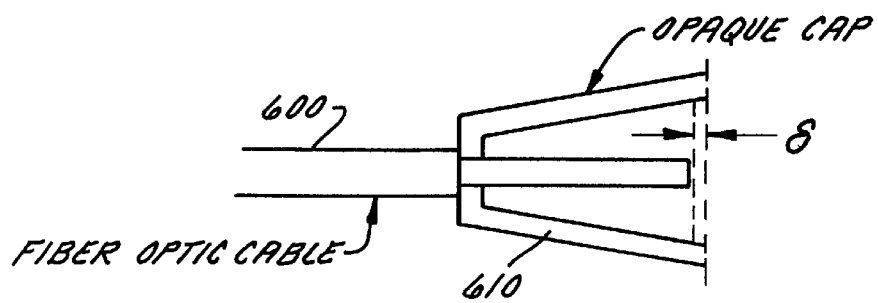
FIG. 5 illustrates a sectional view of a probe according to the present invention.

Each acquired spectrum contains 1100 samples covering wavelengths from 550 nm to 1030 nm. The probe 530 has two functions: transmitting light to the burn area and receiving reflected light from the burn area. The front-view of the probe 530 can be represented as follows: ⊙. The center of the probe 530 can be designed so that it receives reflected light and the surrounding area delivers the source light. Referring to FIG. 5, a black cap 610 covering an optical probe 600 can advantageously prevent light from other sources from entering the probe. Similarly, it can be advantageous to locate the patient within a dark enclosure. A cut-away side-view of the probe is illustrated in FIG. 5, where δ is the distance between the tip of the optical probe 600 and the burn area.

Intelligent analysis and interface software based on the hybrid neural network can be used to operate a low-cost spectrometer and an optimized fiber probe. Thus, general hospitals and emergency units can afford an accurate and reliable system for objective tissue injury classification.

EXAMPLE

A more specific embodiment of the present invention will now be described by the following, nonlimiting example which will serve to illustrate various features of significance. The example is intended merely to facilitate an understanding of ways in which the present invention may be practiced and to further enable those of skill in the art to practice the present invention. Accordingly, the example should not be construed as limiting the scope of the present invention.

To prove the feasibility of the present approach the capability to distinguish between data collected from two types of burns has been clinically demonstrated. The data was collected at the Seattle Burn Center. One set of data represented superficial and the other set of data represented full-thickness skin loss. A hybrid neural network (HNN) including a preprocessing algorithm, a principal components analysis (PCA) procedure, and a multi-layer neural network was used to classify these data sets. The experiment unexpectedly showed 90% accuracy for the examination of 112 samples.

In more detail, a compact spectrometer was used to collect data covering the wavelengths from 500 nm to 1030 nm. A total of 112 samples (spectra) were collected representing 74 cases of superficial and 38 cases of full-thickness skin loss. The data sets were first sorted into two groups. The first group of 56 samples were used for neural network training, and the other 56 samples for testing. Autoscaling was applied to each spectrum so that it has zero mean and unit variance. Then the PCA was employed to produce 10 coefficients from about 1100 data points in each spectrum. The largest ten components were chosen as orthogonal dimension bases. Thus, only ten coefficients remained after PCA instead of 1100 data points in each spectrum. Finally, a BPNN with ten input units, four hidden units, and two output units was trained for about 1500 cycles, producing 51 correct identifications and 5 incorrect responses with the training data set, and 49 correct and 7 incorrect with the testing data set. Thus, the percentage of correct identifications is approximately 90%. Detailed results are shown in Tables I and II. The training time on a 33 MHZ personal computer that implements the BPNN in software was approximately 5 minutes.

TABLE I

| Severity of Burn | Number of Data Sets | Number Correctly Classified | Accuracy |
|---|---|---|---|
| Superficial | 37 | 36 | 97.3% |
| Full-Thickness | 19 | 15 | 78.9% |
| Total | 56 | 51 | 91.1% |

TABLE II

| Severity of Burn | Number of Data Sets | Correct Recognition | Accuracy |
|---|---|---|---|
| Superficial | 37 | 34 | 91.9% |
| Full-Thickness | 19 | 15 | 78.9% |
| Total | 56 | 49 | 87.5% |

Thus, preliminary clinic results using this neural network based instrument unexpectedly showed approximately 90% accuracy in classifying superficial versus deep burn wounds in patients in a Burn Center. This is a significant unexpected improvement over both experienced doctors (whose accuracy is around 50%) and the BDI method (whose accuracy is around 75%).

This example successfully completed a feasibility study of a neural-network-based burn analyzer that is an embodiment of the invention. In this embodiment, a low-cost visible and near infrared (IR) spectrometer was used with a fiber probe to take spectral signals from actual burn patients. An advanced signal processing algorithm was developed to process the data and classify the burns into two categories in real-time.

Needless to say, a practical application of the present invention which has value within the technological arts is objective analysis of wounds such as tissue injuries (e.g., burn injuries). Further, all the disclosed embodiments of the present invention are useful in conjunction with diagnostic techniques such as are used for the purpose of monitoring patients for contusions, bed sores, subdural hematoma, signs of skin cancer, or for the purpose of characterizing biological tissues, blood perfusion, oxygenation and arterial blood gas levels, or the like. The present invention can be used to detect fluorescent markers. The present invention can also be used in industrial process control and environment monitoring. There are virtually innumerable uses for the present invention described herein, all of which need not be detailed here.

Although the best mode contemplated by the inventors of carrying out the present invention is disclosed above, practice of the present invention is not limited thereto. It will be manifest that various additions, modifications and rearrangements of the features of the present invention may be made without deviating from the spirit and scope of the underlying inventive concept.

Moreover, the individual components need not be formed in the disclosed shapes, or assembled in the disclosed configuration, but could be provided in virtually any shape, and assembled in virtually any configuration, which operate together so as to provide objective tissue injury analysis. Further, although the tissue injury analysis equipment described herein is a physically separate module, it will be manifest that the equipment may be integrated into the apparatus with which it is associated. Furthermore, all the disclosed features of each disclosed embodiment can be combined with, or substituted for, the disclosed features of every other disclosed embodiment except where such features are mutually exclusive.

It is intended that the appended claims cover all such additions, modifications and rearrangements. Expedient embodiments of the present invention are differentiated by the appended subclaims.

What is claimed is:

1. An apparatus for assessing an injury to tissue, comprising:
   an electromagnetic signal generator;
   an optical fiber connected to said electromagnetic signal generator;
   a fiber optic probe connected to said optical fiber;
   a broad band spectrometer connected to said fiber optic probe; and
   a hybrid neural network connected to said broad band spectrometer, said hybrid neural network having a plurality of output neurons, each of said plurality of output neurons corresponding to a tissue injury category; and
   wherein said hybrid neural network includes a principle component analyzer of broad band spectral data obtained from said broad band spectrometer; and
   wherein said hybrid neural network produces a set of results at said plurality of output neurons, said set of results indicating the nature of said injury to said tissue.

2. The apparatus of claim 1, wherein said hybrid neural network includes:
   an autoscaling processor;
   a singular value decomposition analyzer; and
   a neural network classifier.

3. The apparatus of claim 1, further comprising an opaque cap operatively connected to said fiber optic probe.

4. The apparatus of claim 1, further comprising a sample enclosure.

5. The apparatus of claim 1, further comprising a positioner operatively connected to said fiber optic probe.

6. An apparatus according to claim 1, wherein one of said plurality of output neurons corresponds to a full thickness burn injury and another of said plurality of output neurons corresponds to a partial thickness burn injury.

7. A method of assessing an injury to tissue, comprising:
   (A) providing
      (1) an electromagnetic signal generator;
      (2) an optical fiber connected to said electromagnetic signal generator;
      (3) a fiber optic probe connected to said optical fiber;
      (4) a broad band spectrometer connected to said fiber optic probe;
      (5) a hybrid neural network connected to said broad band spectrometer, said hybrid neural network having a plurality of output neurons, each of said plurality of output neurons corresponding to a tissue injury category; and
      (6) an output device connected to said hybrid neural network;
   (B) positioning said fiber optic probe proximal an object to be analyzed;
   (C) transmitting a first electromagnetic signal to said object from said electromagnetic signal generator;
   (D) conveying a second electromagnetic signal from said object to said broad band spectrometer;
   (E) transforming said second electromagnetic signal from said object into a broad band spectrum with said broad band spectrometer;
   (F) transmitting said broad band spectrum from said broad band spectrometer to said hybrid neural network;
   (G) processing said broad band spectrum with said hybrid neural network to obtain an autoscaling of said broad band spectrum;
   (H) processing said autoscaling of said broad band spectrum with said hybrid neural network to obtain a principal component analysis of said broad band spectrum by extracting a set of orthogonal feature vectors to represent said broad band spectrum;
   (I) classifying said set of orthogonal feature vectors with said hybrid neural network to produce a set of results at said plurality of output neurons, said set of results indicating the nature of said injury to said tissue; and
   (J) displaying a representation of said set of results using said output device.

8. The method of claim 7, wherein positioning includes contacting said object to be analyzed with said fiber optic probe.

9. The method of claim 7, further comprising repositioning said fiber optic probe and repeating steps (C) through (J) so as to perform imaging spectroscopy.

10. An apparatus for assessing an injury to tissue, comprising:
    an electromagnetic signal generator;
    an optical fiber connected to said electromagnetic signal generator;
    a fiber optic probe connected to said optical fiber;
    a broad band spectrometer connected to said fiber optic probe; and
    a hybrid neural network connected to said broad band spectrometer, said hybrid neural network including:
       a first means for autoscaling broad band spectral data obtained from said broad band spectrometer;
       a means for principal component analysis of broad band spectral data obtained from said broad band spectrometer, said means for principal component analysis including means for performing singular value decomposition analysis;
       a second means for autoscaling data from said means for principal component analysis;
       a neural network classifier; and
       a plurality of output neurons, said plurality of output neurons being disposed at the output of the neural network classifier, each of said plurality of output neurons corresponding to a tissue injury category; and
    wherein said hybrid neural network produces a set of results at said plurality of output neurons, said set of results indicating the nature of said injury to said tissue.

11. The apparatus of claim 10, further comprising an opaque cap operatively connected to said fiber optic probe.

12. The apparatus of claim 10, further comprising a sample enclosure.

13. The apparatus of claim 10, further comprising a positioner operatively connected to said fiber optic probe.

* * * * *

UNITED STATES PATENT AND TRADEMARK OFFICE
CERTIFICATE OF CORRECTION

PATENT NO. : 6,058,352 Page 1 of 1
DATED : May 2, 2000
INVENTOR(S) : Taiwei Lu and Robert A. Lieberman It is certified that error appears in the above-identified patent and that said Letters Patent is hereby corrected as shown below:

<u>Column 1,</u>
Line 4, the following should be inserted:
-- ORIGIN OF THE INVENTION
The invention described herein was made with Government support under contract DAAHO1-96-C-R015 awarded by the U.S. Army Aviation and Missile Command in which the contractor has elected to retain title. --

Signed and Sealed this

Fifteenth Day of July, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,058,352
DATED : May 2, 2000
INVENTOR(S) : Taiwei Lu and Robert A. Lieberman It is certified that error appears in the above-identified patent and that said Letters Patent is hereby corrected as shown below:

Column 1,
Line 4, the following should be inserted:
-- ORIGIN OF INVENTION
The invention described herein was made with Government support under contract DAAHO1-96-C-R015 awarded by the U.S. Army Aviation and Missile Command in which the government has certain rights in the invention. --

Signed and Sealed this

Twenty-eighth Day of September, 2004

JON W. DUDAS
*Director of the United States Patent and Trademark Office*